United States Patent
Hammell

(10) Patent No.: US 10,709,537 B2
(45) Date of Patent: Jul. 14, 2020

(54) SURGICAL PATCH COVER AND METHOD OF USE

(71) Applicant: Covidien LP, Mansfield, MA (US)

(72) Inventor: Eugene J. Hammell, McMurray, PA (US)

(73) Assignee: Covidien LP, Mansfield, MA (US)

( * ) Notice: Subject to any disclaimer, the term of this patent is extended or adjusted under 35 U.S.C. 154(b) by 368 days.

(21) Appl. No.: 15/811,723

(22) Filed: Nov. 14, 2017

(65) Prior Publication Data

US 2018/0064523 A1 Mar. 8, 2018

Related U.S. Application Data

(63) Continuation of application No. 13/319,219, filed as application No. PCT/US2010/033673 on May 5, 2010, now Pat. No. 9,814,556.

(60) Provisional application No. 61/176,157, filed on May 7, 2009.

(51) Int. Cl.
*A61F 2/00* (2006.01)
*D04B 21/16* (2006.01)

(52) U.S. Cl.
CPC .......... *A61F 2/0063* (2013.01); *D04B 21/16* (2013.01); *A61F 2/0077* (2013.01); *A61F 2/0095* (2013.01); *A61F 2220/0016* (2013.01); *D10B 2501/0632* (2013.01); *D10B 2509/08* (2013.01)

(58) Field of Classification Search
CPC ............ A61F 2/0063; A61F 2002/0068; A61F 2013/00089; A61F 2013/00127; A61F 13/00004; A61F 13/00008; A61F 13/00012; D04B 21/16; D10B 2509/08; D10B 2509/0631; D10B 2509/0632
See application file for complete search history.

(56) References Cited

U.S. PATENT DOCUMENTS 5,290,217 A    3/1994 Campos
5,716,409 A *  2/1998 Debbas ................. A61F 2/0063
                                                   606/151
6,166,286 A   12/2000 Trabucco
(Continued)

FOREIGN PATENT DOCUMENTS

WO    2008140439 A1    11/2008

OTHER PUBLICATIONS

Hay et al., Shouldice Inguinal Hernia Repair in the Male Adult: The Gold Standard?, Annals of Surgery, vol. 222, No. 6 (Dec. 1995), 719-727.

(Continued)

*Primary Examiner* — Wade Miles
(74) *Attorney, Agent, or Firm* — Weber Rosselli & Cannon LLP

(57) ABSTRACT

A device for performing surgery on a patient includes: a mesh patch comprising a top surface and a bottom surface; and a removable cover positioned adjacent to and in facing engagement with the bottom surface of the mesh patch. The bottom surface has a plurality of hooks positioned thereon. The cover is removed from the mesh patch as the mesh patch is positioned at a surgical site such that the hooks on the bottom of the mesh patch grip surrounding tissue of a patient and secure the mesh patch to surrounding tissue of the surgical site. A method for performing a surgery using such a device is also provided.

20 Claims, 9 Drawing Sheets

(56) References Cited

U.S. PATENT DOCUMENTS

| | | | |
|---|---|---|---|
| 6,174,320 B1* | 1/2001 | Kugel | A61F 2/0063 606/151 |
| 6,241,768 B1 | 6/2001 | Agarwal et al. | |
| 6,565,580 B1 | 5/2003 | Beretta | |
| 6,610,006 B1* | 8/2003 | Amid | A61F 2/0063 600/37 |
| 6,991,643 B2* | 1/2006 | Saadat | A61B 17/08 606/221 |
| 7,413,570 B2* | 8/2008 | Zamierowski | A61B 17/064 602/41 |
| 7,662,169 B2* | 2/2010 | Wittmann | A61B 17/00234 606/215 |
| 7,828,854 B2* | 11/2010 | Rousseau | A61F 2/0063 623/23.72 |
| 8,062,331 B2* | 11/2011 | Zamierowski | A61B 17/064 602/43 |
| 8,858,577 B2* | 10/2014 | Kubiak | A61B 17/1114 606/151 |
| 9,814,556 B2 | 11/2017 | Hammell | |
| 2001/0044637 A1 | 11/2001 | Jacobs et al. | |
| 2001/0049538 A1 | 12/2001 | Trabucco | |
| 2002/0013590 A1 | 1/2002 | Therin et al. | |
| 2002/0029063 A1* | 3/2002 | Wittmann | A61B 17/00234 606/215 |
| 2003/0130745 A1* | 7/2003 | Cherok | A61F 2/0063 623/23.72 |
| 2004/0019360 A1 | 1/2004 | Farnsworth et al. | |
| 2005/0192600 A1 | 9/2005 | Nicolo et al. | |
| 2005/0234510 A1* | 10/2005 | Zamierowski | A61B 17/064 606/215 |
| 2006/0025785 A1 | 2/2006 | Cully et al. | |
| 2008/0154366 A1* | 6/2008 | Frank | A61F 2/0063 623/8 |
| 2008/0161837 A1 | 7/2008 | Toso et al. | |
| 2008/0167668 A1 | 7/2008 | Criscuolo et al. | |
| 2008/0188936 A1* | 8/2008 | Ball | A61B 17/1146 623/13.14 |
| 2008/0243149 A1* | 10/2008 | Kockerling | A61F 2/0063 606/151 |
| 2009/0012350 A1* | 1/2009 | Tihon | A61B 17/282 600/30 |
| 2009/0030434 A1 | 1/2009 | Paz et al. | |
| 2009/0069904 A1 | 3/2009 | Picha | |
| 2012/0179175 A1* | 7/2012 | Hammell | A61F 2/0063 606/151 |

OTHER PUBLICATIONS

Miedema et al., A Prospective Trial of Primary Inguinal Hernia Repair by Surgical Trainees, Hernia (2004) 8: 28-32.
International Search Report dated Jul. 13, 2010 in corresponding International Application No. PCT/2010/033673.
Written Opinion of the International Searching Authority dated Jul. 13, 2010 in corresponding International Application No. PCT/2010/033673.
Canadian Office Action dated May 3, 2016 in corresponding Canadian Patent Application No. 2,761,312, 3 pages.

* cited by examiner

SURGICAL PATCH COVER AND METHOD OF USE

CROSS-REFERENCE TO RELATED APPLICATIONS

This application is a Continuation of U.S. patent application Ser. No. 13/319,219 filed Mar. 28, 2012, which is a National Stage Application of PCT/US10/33673 filed May 5, 2010, which claims benefit of and priority to U.S. Provisional Application No. 61/176,157 filed May 7, 2009, and the disclosures of each of the above-identified applications are hereby incorporated by reference in their entirety.

BACKGROUND OF THE INVENTION

1. Field of the Invention

The present invention, in general, is directed to a mesh patch for surgical procedures and, more particularly, to a cover for such mesh patches and methods of performing surgeries with such mesh patches.

2. Description of Related Art

The groin is one of the natural weak areas in the abdominal wall and is the most common site for abdominal herniation. In particular, inguinal hernias are defined as those occurring above the abdominocrural crease. Inguinal hernias are usually classified as direct or indirect. The sac of an indirect inguinal hernia passes obliquely or indirectly toward and ultimately into the scrotum. The sac of a direct inguinal hernia protrudes directly outward and forward. Clinically distinguishing an indirect from a direct inguinal hernia is often impossible and is of little importance since the operation to repair them is substantially the same.

Traditionally, inguinal hernias have been repaired via one of two types of operative procedure. A first technique is a laparoscopic approach which requires the patient to be under a general anesthetic. However, this approach is less preferred because it has a high early recurrence rate and a steep learning curve for the surgeon. A more preferred approach is called an "open technique" in which a small two (2) to three (3) inch incision is made in the inguinal area after the patient is under local, regional, or general anesthesia and the hernia is repaired.

In order to enhance the "open technique", surgically implantable mesh patches for the repair of inguinal and other abdominal wall hernias have been provided. Tension free surgical repairs of hernias have been developed using synthetic mesh materials to bridge and to patch hernia defects. Repairs utilizing such surgically implantable mesh patches resulted in both a decrease in the recurrence rate as well as a decrease in the amount of a patient's post operative discomfort. Patients undergoing these more advanced procedures were able and are able to resume their normal activities sooner.

With reference to FIGS. 1 through 3, an example of such a mesh patch, denoted generally as reference numeral 1, is the Paritex ProGrip™ Mesh manufactured by Covidien AG, 150 Glover Avenue, Norwalk, Conn. 06856. Mesh patch 1 has, viewed from above, the general shape of an ellipse. This ellipse includes a lower edge 3a and an upper edge 3b with a large radius of curvature and two lateral edges 3c, 3d with a small radius of curvature. The shape of upper edge 3b is specifically adapted to the anterior inguinal region and more precisely to the space formed after opening of the aponeurosis of the external oblique muscle, access to the conjoined tendon and the aponeurosis of the rectus muscle, the latter being fixed between the insertion of the aponeurosis of the external oblique muscle and that of the rectus muscle. This anatomical asymmetry combined with the presence of a flap 5 means mesh patch 1 can provide either a right reinforcement or a left reinforcement. Mesh patch 1 shown in FIG. 1 is a right reinforcement (relative to the patient). The large curvature of lower edge 3a allows a perfect match to the crural arch as far as the pubis.

Mesh patch 1 also includes a slit 7 positioned perpendicular to upper edge 3b and extending substantially over half of the width of mesh patch 1. The inner end of slit 7 opens into an orifice 9 which is cylindrical and which, for example, has a diameter of 3 to 7 millimeters. Flap 5 has a shape of a sector of a circular annulus and is connected via one of its radial edges to one of the edges of mesh patch 1 which delimits the slit 7. Flap 5 is joined to mesh patch 1 in such a way that the concavity of its inner and outer arched edges is directed towards orifice 9.

Mesh patch 1 is made of a sheet of low-weight monofilament polyester knitted fabric 11 having a top surface 13 and a bottom surface 15. The polyester knitted fabric 11 has a low weight isoelastic structure with large pores as shown in FIG. 2. In addition, polyester knitted fabric 11 incorporates resorbable polylactic acid (PLA) micro-hooks 17 on bottom surface 15 thereof. Resorbable PLA micro-hooks 17 provide self-gripping properties to mesh patch 1 during a procedure and the first month post-implantation. Mesh patch 1 is configured to be secured around a spermatic cord of the patient using flap 5. Flap 5 is made of the same fabric as mesh patch 1 (i.e., polyester with polylactic acid micro-hooks knitted fabric), thereby providing it with self-gripping properties. After complete tissue ingrowth and complete resorption of PLA micro-hooks 17, mesh patch 1 ensures long term abdominal wall reinforcement.

However, the implantation of such a patch can be challenging. More particularly, during implantation using the recommended procedure, PLA micro-hooks 17 of mesh patch 1 can stick to tissue surrounding the implantation site and may need to be removed from such tissue. As mesh patch 1 is removed, the fragile PLA micro-hooks can be torn from bottom surface 15 of mesh patch 1. Accordingly, once mesh patch 1 arrives at the desired location, most, if not all, of the PLA micro-hooks 17 may be disengaged from bottom surface 15 of mesh patch 1, and the surgeon may be required to stitch mesh patch 1 in position. In addition, if flap 5 is positioned too loose or tight around the patient's spermatic cord various problems can arise. For instance, positioning flap 5 too tightly around the spermatic cord can lead to testicular ischemia whereas positioning flap 5 too loosely around the spermatic cord can lead to a recurrent hernia.

Accordingly, a need exists for a removable cover for mesh patch 1 that prevents PLA micro-hooks 17 from securing themselves to surrounding tissue during implantation of mesh patch 1. In addition, a need exists for a surgical method of implanting mesh patch 1 using such a cover.

SUMMARY OF THE INVENTION

In some embodiments the present invention provides a surgical combination having a removable cover for a mesh patch that prevents the micro-hooks of the mesh patch from securing themselves to surrounding tissue during implantation of the patch. Another aspect of the present invention is to provide a surgical method of implanting a mesh patch using such a cover.

The present invention provides a device for performing surgery on a patient. The device comprises: a mesh patch comprising a top surface and a bottom surface; and a removable cover positioned adjacent to and in facing engagement with the bottom surface of the mesh patch. The bottom surface has a plurality of hooks positioned thereon. The cover is removed from the mesh patch as the mesh patch is positioned at a surgical site such that the hooks on the bottom of the mesh patch grip surrounding tissue of a patient and secure the mesh patch to surrounding tissue of the surgical site.

The present invention also provides a surgical combination that comprises a mesh patch having a top surface and a bottom surface; and a removable cover positioned adjacent to and in facing engagement with the bottom surface of the mesh patch. The bottom surface has a plurality of hooks positioned thereon. The cover is removed from the mesh patch as the mesh patch is positioned at a surgical site such that the hooks on the bottom of the mesh patch grip surrounding tissue of a patient and secure the mesh patch to surrounding tissue of the surgical site.

The present invention is further directed to a kit for surgical repair. The kit comprises a mesh patch comprising a top surface and a bottom surface; and a removable cover configured to be positioned adjacent to and in facing engagement with the bottom surface of the mesh patch. The bottom surface has a plurality of hooks positioned thereon. The cover is removed from the mesh patch as the mesh patch is positioned at a surgical site such that the hooks on the bottom of the mesh patch grip surrounding tissue of a patient and secure the mesh patch to surrounding tissue of the surgical site. The kit may further comprise an additional sheet of polymeric material configured to be cut into pieces by a surgeon to line the surgical site prior to positioning the cover and patch.

The present invention also provides a method for repairing an abdominal wall hernia. The method includes the steps of: a) cutting a transverse oblique incision in a fold of a groin of a patient; b) widely dissecting a superficial inguinal space of the patient, thereby freeing fascial surfaces and creating a surgical site; c) mobilizing a spermatic cord of the patient using a latex band; d) repairing the abdominal wall hernia and making a relaxing incision in an internal oblique fascia of the patient; e) providing a device that includes a mesh patch with a top surface and a bottom surface having a plurality of hooks positioned thereon; and a removable cover having a first side positioned on the bottom surface of the mesh patch; f) positioning the device over the surgical site such that a second side of the cover is adjacent to the surgical site; g) removing the cover as the mesh patch is positioned at the surgical site such that the hooks on the bottom of the mesh patch grip the surrounding tissue and secure the mesh patch to the surgical site; and h) closing the incision with stitches. The method may further comprise the step of lining the surgical site with pieces of a sheet of polymeric material prior to step e).

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

DETAILED DESCRIPTION OF THE PRESENT INVENTION

Figure 1:
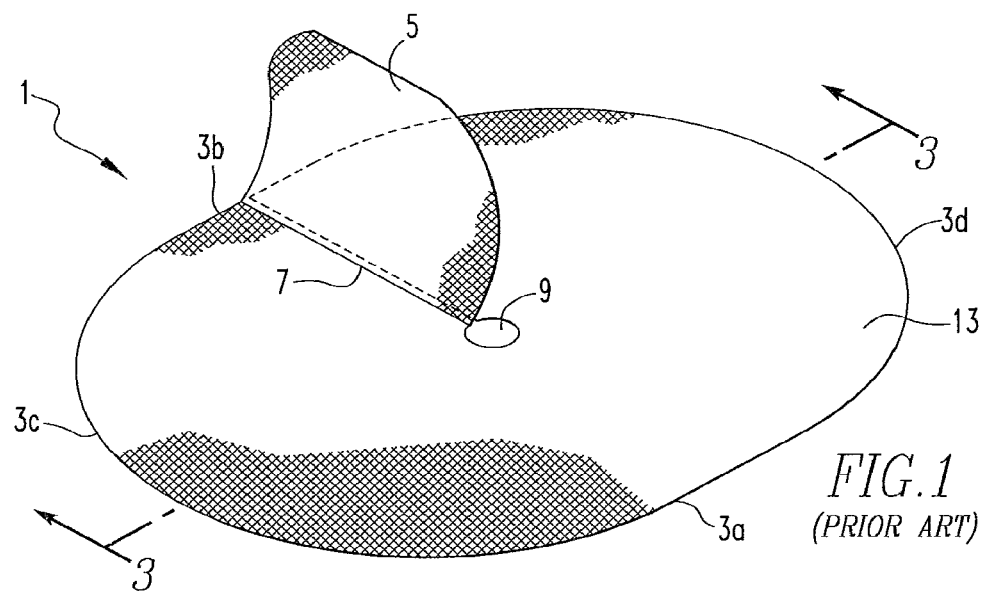
FIG. 1 is a perspective view of a conventional mesh patch for use in repairing abdominal wall hernias.
Figure 2:
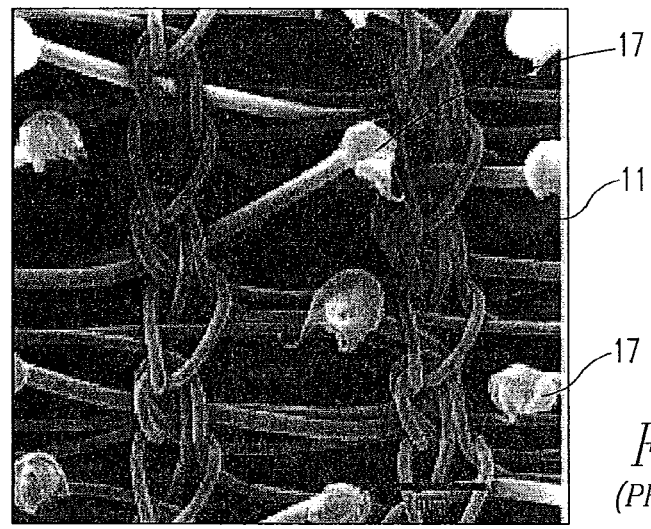
FIG. 2 is a magnified photographic view of the bottom surface of the mesh patch of FIG. 1.
Figure 3:
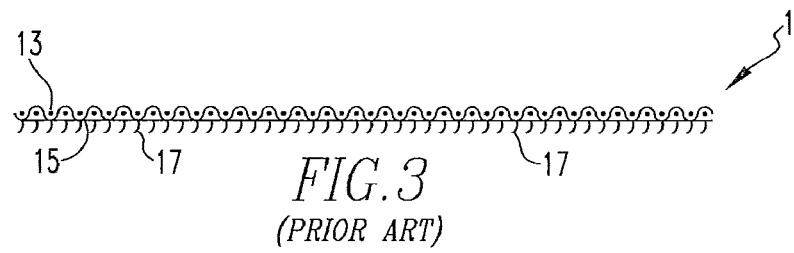
FIG. 3 is a cross-sectional view of the mesh patch of FIG. 1 taken along line 3-3.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 4:
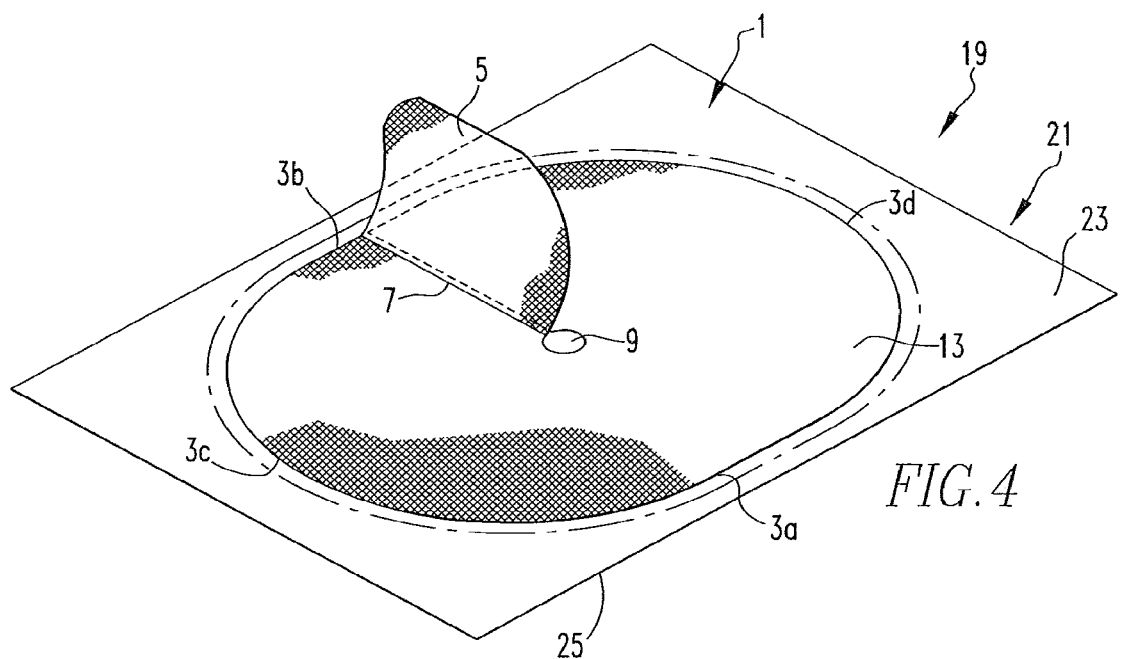
FIG. 4 is a perspective view of a device for performing surgery on a patient in accordance with the present invention.

With reference to FIG. 4, a device, denoted generally as reference numeral 19, for performing surgery comprises a mesh patch 1 as described hereinabove; and a removable cover, denoted generally as reference numeral 21.

While the mesh patch configuration is discussed with respect to a patch for hernia repair, one skilled in the art will understand that the shape of the patch can vary, depending upon the surgical procedure to be performed, and may or may not include a flap. The mesh patch 1 comprises a top surface 13 and a bottom surface 15 opposite the top surface 13. In some non-limiting embodiments, mesh patch 1 can have a generally ellipse-like shape that includes a lower edge 3a and an upper edge 3b with a large radius of curvature and two lateral edges 3c, 3d with a small radius of curvature. A slit 7 is positioned perpendicular to upper edge 3b and extending substantially over half of the width of mesh patch 1. The inner end of slit 7 opens into an orifice 9. A flap 5 having a shape of a sector of a circular annulus is also provided and is connected via one of its radial edges to one of the edges of mesh patch 1 which delimits the slit 7.

Mesh patch 1 can be made of a sheet of low-weight monofilament polyester knitted fabric 11 having a top surface 13 and a bottom surface 15. However, this is not to be construed as limiting the present invention as any suitable material, for example, a plastic material such as polypropylene, may be used. Mesh patch 1 also comprises a plurality of hooks 17. In addition, polyester knitted fabric 11 incorporates bioresorbable polylactic acid (PLA) microhooks 17 on bottom surface 15 thereof Removable cover 21 has a top side 23 and a bottom side 25. Top side 23 of cover 21 is configured to be positioned adjacent to and in facing engagement with bottom surface 15 of mesh patch 1. Bottom side 25 is configured to be positioned adjacent to a surgical site as will be discussed in greater detail hereinafter. Removable cover 21 may be of any suitable size such that it completely covers bottom surface 15 of mesh patch 1. For example, if mesh patch 1 has an elliptical shape that is 12 cm by 8 cm, the removable cover 21 may be of a rectangular or elliptical shape that is 15 cm by 9 cm. In addition, removable cover 21 may have a thickness in the range of 0.005 mm to 1 mm.

Removable cover 21 is provided as a layer of sterile, smooth polymeric material such as a polymer film manufactured from polyolefins, such as polypropylene. Desirably, removable cover 21 is prepared from the same material as the inner, sterile liner of esteem SMT non-porous, powder-free, latex-free surgical gloves distributed by Cardinal Health, McGaw Park, Ill. 60085. As shown in FIG. 4, device 19 may be manufactured and sold as a combination. Alternatively, mesh patch 1 and removable cover 21 may be sold as individual components and used in combination.

Figure 5:
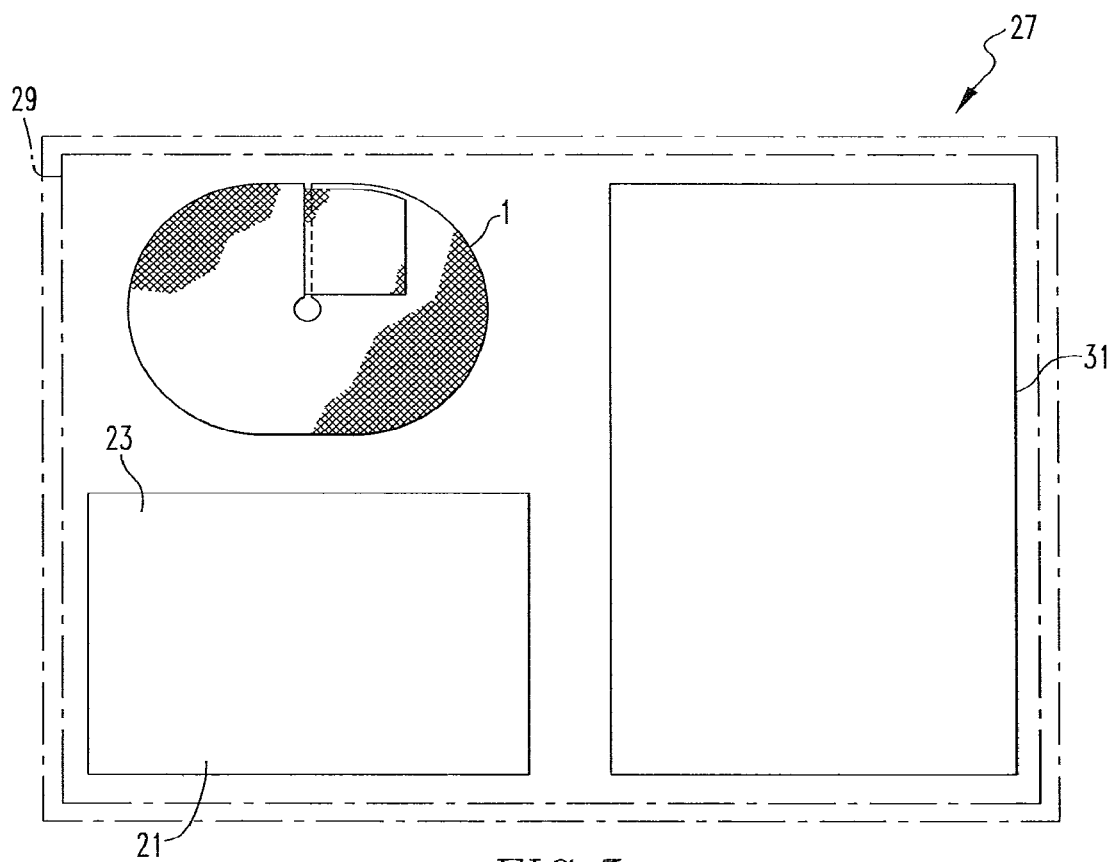
FIG. 5 is a top plan view of a kit for use in performing a surgical repair in accordance with the present invention.
Figure 6:
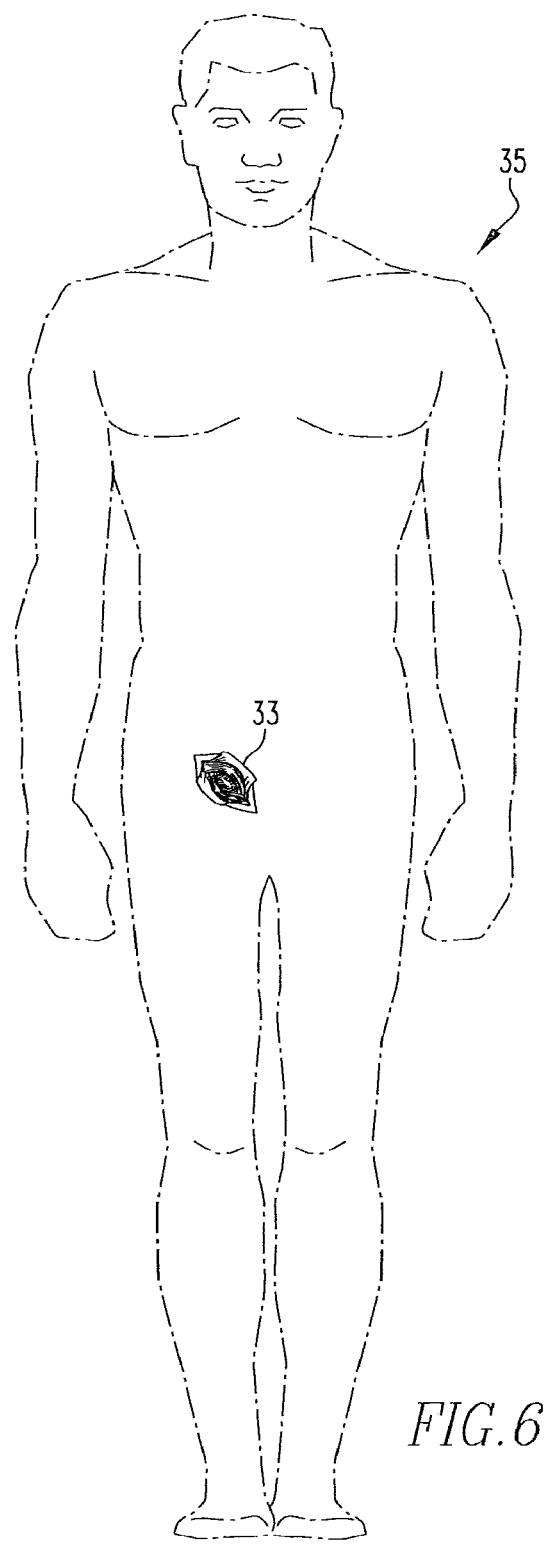
FIG. 6 is a schematic front view of a patient's body indicating, in respect to the surgical repair of an inguinal hernia, where an incision is made in a fold of a groin of the patient.
Figure 7:
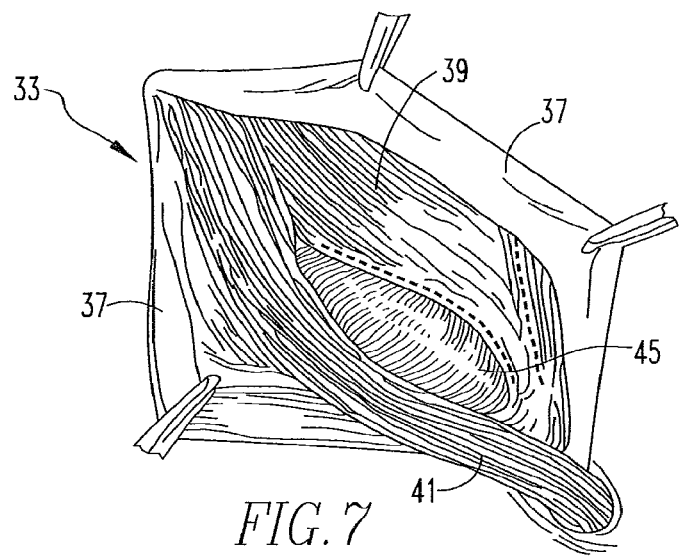
FIGS. 7 through 14 illustrate the various steps of a method for repairing an inguinal hernia using the device of the present invention.
Figure 8:
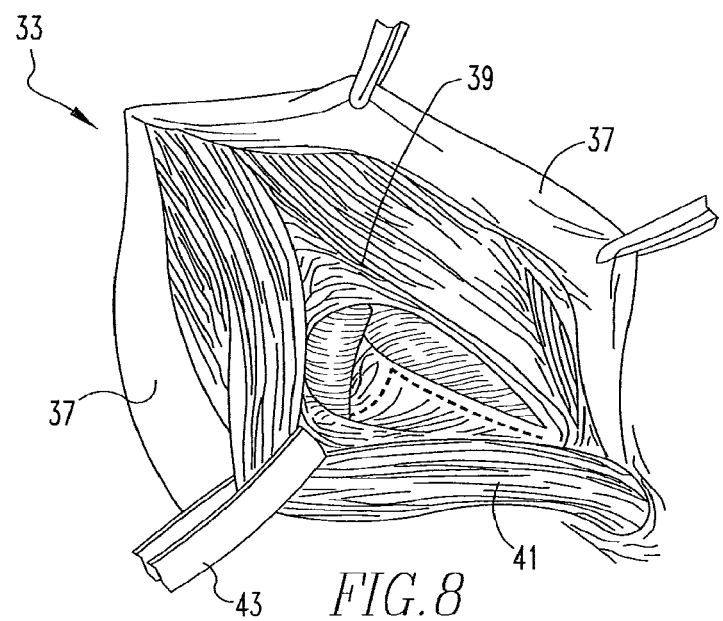
Figure 9:
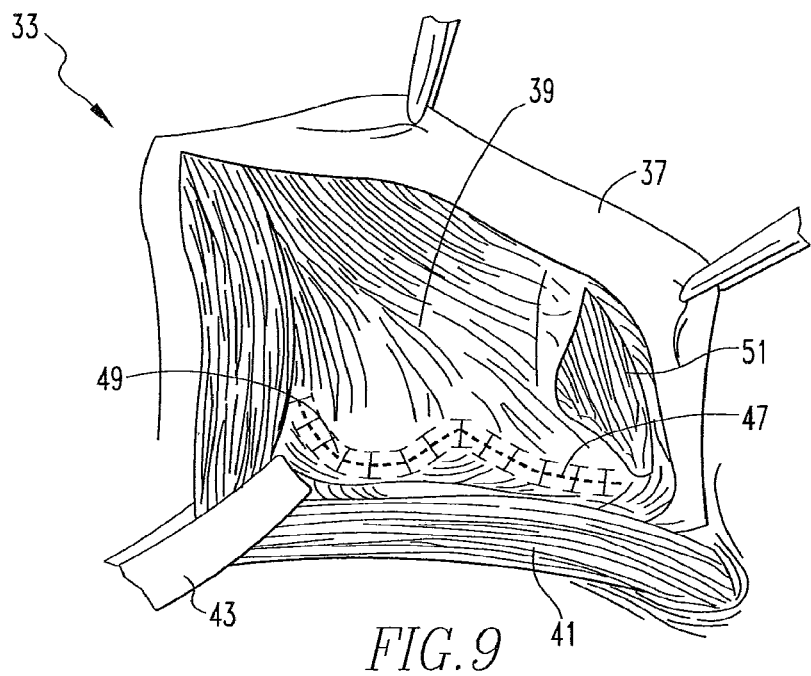

In addition, and as shown in FIG. 5, mesh patch 1 and removable cover 21 may be sold in a kit, denoted generally as reference numeral 27. Kit 27 includes mesh patch 1 and removable cover 21 provided in a package 29. Package 29 may also include one or more additional sheet(s) 31 of sterile, polymeric material configured to be cut into pieces by a surgeon to line the surgical site prior to positioning the combination of removable cover 21 and mesh patch 1. Sheet 31 can be prepared from any sterile surgical polymer material, and can be prepared from the same polymeric material as removable cover 21, if desired. While an exemplary embodiment of kit 27 is illustrated in FIG. 5, this is not to be construed as limiting the present invention as any number of configurations for kit 27 has been envisioned.

With reference to FIGS. 6-14, and with continuing reference to FIGS. 4 and 5, the method for repairing an inguinal hernia using device 19 and/or kit 27 of the present invention is described hereinafter. While the following description is provided for the repair of an inguinal hernia, the device of the present invention is not limited to use in repairing inguinal hernias. Different shapes and sizes of mesh patch 1 and removable cover 21 may be provided to perform various types of surgery where mesh patches are used, such as laparoscopic ventral hernia repair, diaphragmatic hernia repair, and soft tissue reconstruction.

The repair of an inguinal hernia in accordance with the procedure of the present invention begins with the cutting of a transverse oblique incision 33 in a fold of a groin of a patient 35. Thereafter, a superficial inguinal space of patient 35 is widely dissected, thereby freeing fascial surfaces 37 and creating a surgical site 39 (see FIG. 7). Next, the spermatic cord 41 of patient 35 is mobilized using a latex band 43 (see FIG. 8). In some instances, latex band 43 may be covered with a piece of polymeric material cut from additional sheet 31.

The surgeon then identifies a hernia sac (indirect hernia) or a hernia bulge (direct hernia), and repairs the hernia. Thereafter, a relaxing incision 51 in the internal oblique fascia is made by the surgeon to reduce tension in this area. For an indirect hernia, the surgeon tightens the internal inguinal ring with an absorbable stitch. For a direct hernia, the hernia sac 45 is imbricated to temporarily reduce the hernia bulge and then the superior and medial portion of the transverse layer is drawn downward and sutured to the superior pubic ligament as denoted by reference numeral 47 and to the anterior femoral sheath as denoted by reference numeral 49 (see FIG. 9).

Figure 10:
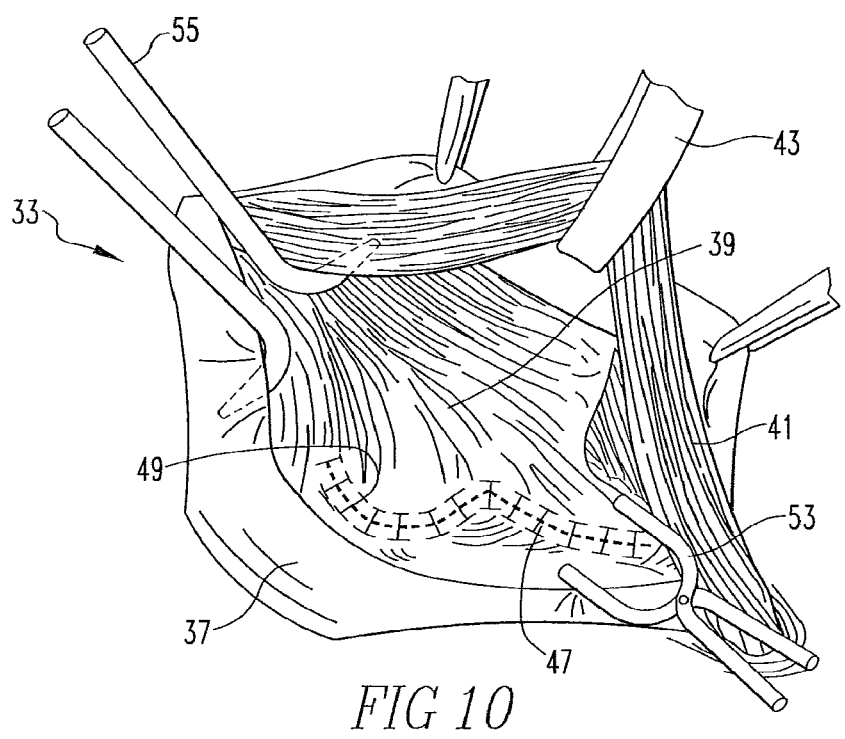
Figure 11:
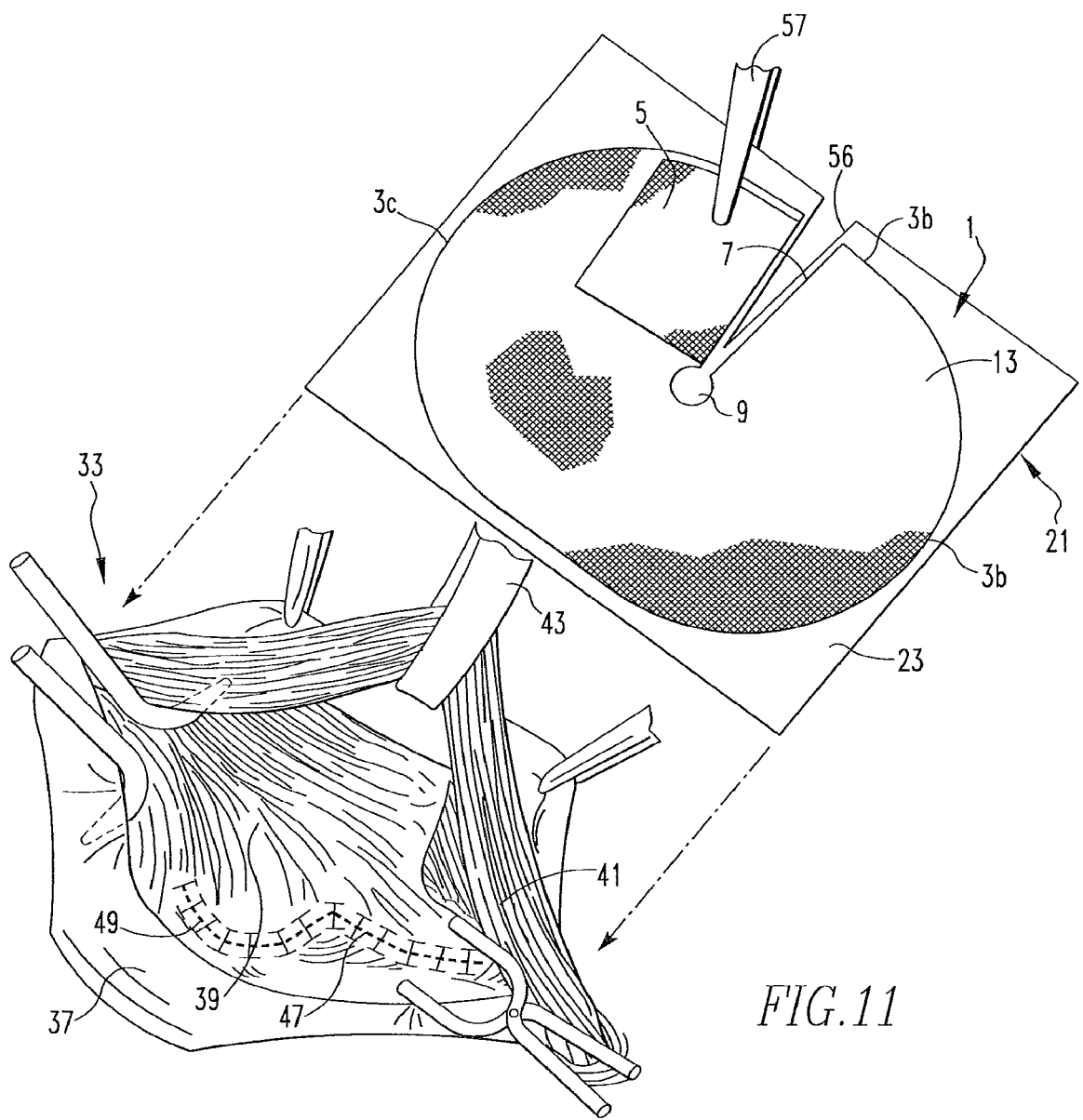
Figure 12:
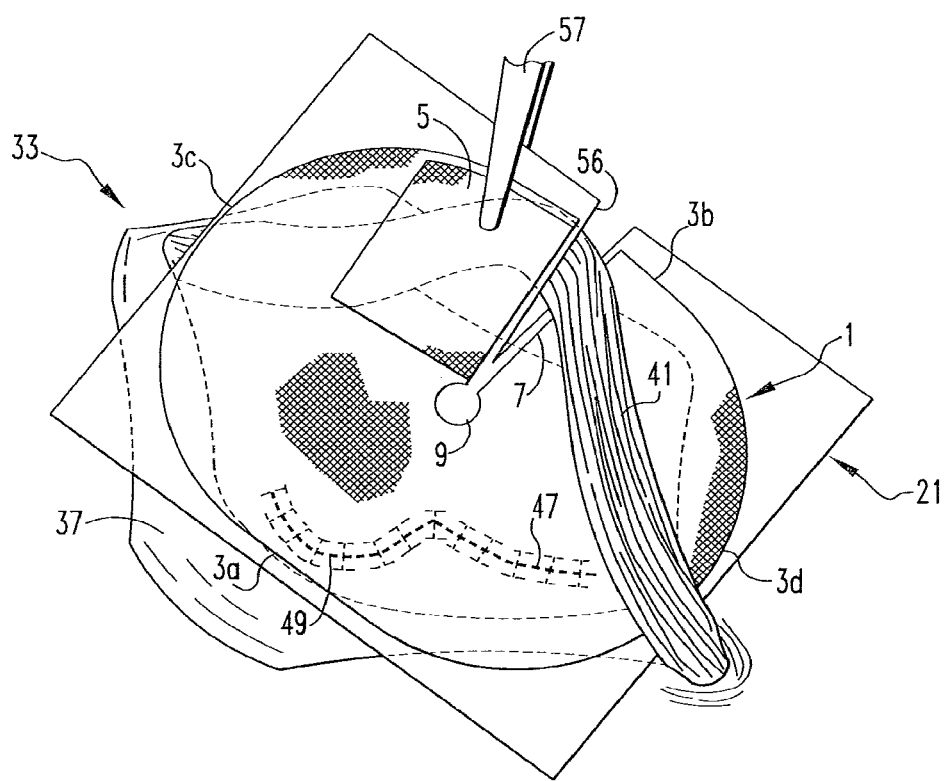
Figure 13:
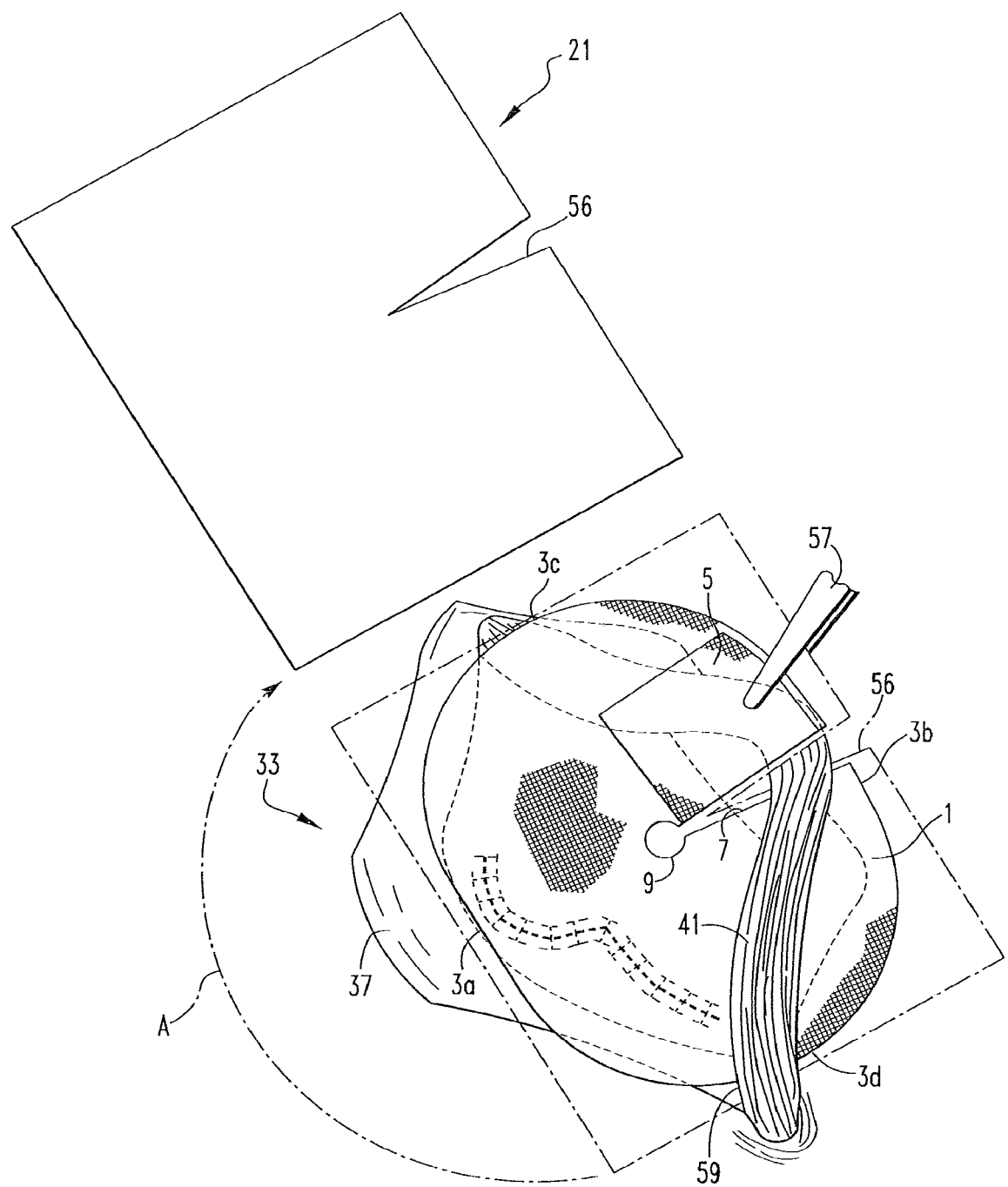

As shown in FIG. 10, the surgeon then increases the size of surgical site 39 using a flag retractor 53 and a Gelpi retractor 55. In addition, at this point in the surgical procedure, the surgeon also may line surgical site 39 with pieces cut from additional sheet 31 of polymeric material. Then, device 19 of the present invention is positioned over surgical site 39 such that bottom side 25 of removable cover 21 is adjacent to surgical site 39 (see FIGS. 11 and 12). As discussed hereinabove, device 19 may be provided as a prepackaged unit, as a kit, or as separate cover 21 and mesh patch 1 components.

Removable cover 21 covers micro-hooks 17 until the surgeon maneuvers mesh patch 1 into a proper position, thereby avoiding accidental exposure of micro-hooks 17 to prevent premature fixation to structures that destroy the fragile nature of micro-hooks 17. A slit 56 may be cut into cover 21 to correspond with slit 7 provided in mesh patch 1. Flap 5 is folded on itself and held temporarily open with an Alice clamp 57. Alice clamp 57 looks like a hemostat but has "c"-shaped tips that only contact a very small surface area so as to not crush too many micro-hooks 17.

Next, the surgeon directs mesh patch 1 medially over the pubic tubercle 59 such that slit 7 of mesh patch 1 is toward the patient's head and flap 5 is open. Once mesh patch 1 is in position, removable cover 21 is slid laterally in the direction of arrow A to expose bottom surface 15 and micro-hooks 17 of mesh patch 1 to surgical site 39 (see FIG. 13). The surgeon then gently presses mesh patch 1 into pubic tubercle 59 overlapping the inguinal ligament, and extends mesh patch 1 to cover relaxing incision 51. Desirably, an assistant exerts an upward pressure on the surrounding tissue with a Richardson (blunt) retractor (not shown). Thereafter, the surgeon continues to slide cover 21 laterally along the inguinal ligament in the direction of arrow A while moving the retractor to the lateral border of incision 33. Once edges 3a and 3d of mesh patch 1 have been fixed, the remainder of mesh patch 1 is properly positioned around spermatic cord 41. In some instances, the surgeon may need to place stitches along the border of the inguinal ligament to assure mesh patch 1 does not move.

Figure 14:
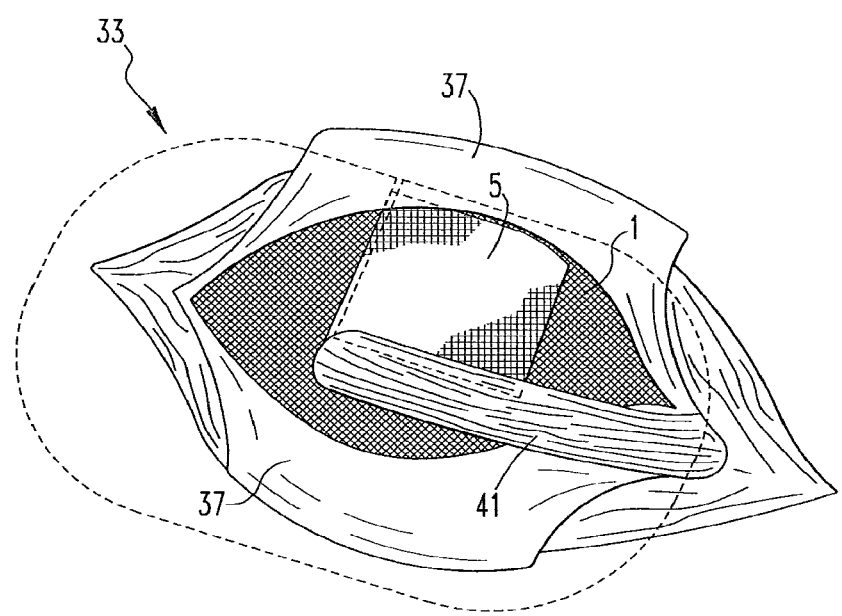

The final step in positioning mesh patch 1 is to remove Alice clamp 57 and to close flap 5 around spermatic cord 41, thus creating a new internal ring that is completely tension free and custom made (see FIG. 14). Once mesh patch 1 is in place, all pieces of additional sheet 31 that may have been placed in incision 33 are removed along with any latex bands (around the spermatic cord). The external fascial surfaces 37 are then closed with an absorbable stitch, and the skin is also closed with an absorbable stitch.

Although the invention has been described in detail for the purpose of illustration based on what is currently considered to be the most practical embodiments, it is to be understood that such detail is solely for that purpose and that the invention is not limited to the disclosed embodiments, but, on the contrary, is intended to cover modifications and equivalent arrangements. For example, it is to be understood that the present invention contemplates that, to the extent possible, one or more features of any embodiment can be combined with one or more features of any other embodiment.

What is claimed is:

1. A device for performing surgery on a patient, the device comprising:

a mesh patch comprising a top surface and a bottom surface, the bottom surface having a plurality of hooks positioned thereon; and a removable cover comprising a top side and a bottom side, the top side configured to be positioned adjacent to and in facing engagement with the bottom surface of the mesh patch and the bottom side configured to be positioned adjacent to a surgical site, the removable cover further comprising a non-porous polymeric material, wherein the top surface of the mesh patch is uncovered and the removable cover is configured to be removed from the bottom surface of the mesh patch as the mesh patch is positioned at a surgical site such that the hooks on the bottom surface of the mesh patch grip surrounding tissue of a patient and secure the mesh patch to surrounding tissue of the surgical site.

2. The device of claim 1, wherein the mesh patch comprises polyester, polypropylene, polylactic acid, or any combination thereof.

3. The device of claim 1, wherein the hooks comprise a bioresorbable material.

4. The device of claim 3, wherein the hooks comprise polylactic acid.

5. The device of claim 1, wherein the polymeric material comprises a polymeric film.

6. The device of claim 5, wherein the polymeric film comprises a single layer of non-porous polymeric material.

7. The device of claim 1, wherein the surgical site is a portion of an abdominal wall in a groin area of a patient.

8. A kit for surgical repair comprising:

a mesh patch comprising a top surface and a bottom surface, the bottom surface having a plurality of hooks positioned thereon; and a removable cover a top side and a bottom side, the top side configured to be positioned adjacent to and in facing engagement with the bottom surface of the mesh patch and the bottom side configured to be positioned adjacent to a surgical site, the removable cover further comprising a non-porous polymeric material, wherein the top surface of the mesh patch is uncovered and the removable cover is configured to be removed from the bottom surface of the mesh patch as the mesh patch is positioned at a surgical site such that the hooks on the bottom surface of the mesh patch grip surrounding tissue of a patient and secure the mesh patch to surrounding tissue of the surgical site.

9. The kit of claim 8, further comprising an additional sheet of polymeric material.

10. The kit of claim 9, wherein the additional sheet is configured to be cut into pieces by a surgeon to line the surgical site prior to removing the cover from the mesh patch.

11. The kit of claim 8, wherein the mesh patch comprises polyester, polypropylene, polylactic acid or any combination thereof.

12. The kit of claim 8, wherein the hooks comprise a bioresorbable material.

13. The kit of claim 12, wherein the hooks comprise polylactic acid.

14. The kit of claim 8, wherein the removable polymeric material comprises a polymeric film.

15. The kit of claim 14, wherein the polymeric film comprises a single layer of non-porous polymeric material.

16. A method for repairing an abdominal wall hernia comprising the steps of:
a) forming a surgical incision in a groin area of a patient;
b) dissecting a superficial inguinal space of the patient, thereby freeing fascial surfaces and creating a surgical site;
c) repairing the abdominal wall hernia
d) positioning a device over the surgical site, the device comprising a mesh patch comprising a top surface and a bottom surface, the bottom surface having a plurality of hooks positioned thereon; and a one-piece removable cover including a non-porous polymeric film layer, the removable cover having a top side positioned on the bottom surface of the mesh patch and a bottom side positioned adjacent the surgical site;
e) sliding the one-piece removable cover laterally across the surgical site and the bottom surface of the mesh patch exposing the hooks on the bottom surface of the mesh patch to grip surrounding tissue to secure the bottom surface of the mesh patch to the surgical site; and
f) closing the surgical incision.

17. The method of claim 16, further comprising the step of lining the surgical site with pieces of an additional sheet of polymeric material prior to step d).

18. The method of claim 16, further comprises the step of mobilizing a spermatic cord of the patient using a latex band prior to repairing the abdominal wall hernia of step c).

19. The method of claim 16, wherein the polymeric film layer comprises a single layer.

20. A surgical combination comprising:

a mesh patch comprising a top surface and a bottom surface, the bottom surface having a plurality of absorbable hooks positioned thereon; and a one-piece removable cover comprising a single non-porous polymeric film layer positioned adjacent to and in facing engagement with the bottom surface of the mesh patch, wherein the one-piece removable cover is configured to protect the absorbable hooks prior to implantation and slide laterally across the absorbable hooks to expose the absorbable hooks upon implantation to grip to surrounding tissue of a surgical site.

* * * * *